(12) United States Patent
Horiuchi et al.

(10) Patent No.: US 11,747,492 B2
(45) Date of Patent: Sep. 5, 2023

(54) RADIOGRAPHY APPARATUS

(71) Applicant: FUJIFILM CORPORATION, Tokyo (JP)

(72) Inventors: Hisatsugu Horiuchi, Kanagawa (JP); Kotatsu Kawaguchi, Kanagawa (JP); Masateru Tateishi, Kanagawa (JP); Shinsuke Noguchi, Kanagawa (JP); Daisuke Ogawa, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 150 days.

(21) Appl. No.: 17/458,482

(22) Filed: Aug. 26, 2021

(65) Prior Publication Data

US 2022/0099847 A1 Mar. 31, 2022

(30) Foreign Application Priority Data

Sep. 28, 2020 (JP) .................. 2020-162672

(51) Int. Cl.
*G01T 1/20* (2006.01)
*A61B 6/00* (2006.01)

(52) U.S. Cl.
CPC .......... *G01T 1/2019* (2020.05); *A61B 6/4283* (2013.01); *A61B 6/4405* (2013.01); *G01T 1/20189* (2020.05)

(58) Field of Classification Search
CPC .......................... G01T 1/2019; G01T 1/20189
See application file for complete search history.

(56) References Cited

U.S. PATENT DOCUMENTS

2007/0123133 A1* 5/2007 Winters ............ H10K 71/00
445/24
2018/0313961 A1* 11/2018 Ushikura ............ H01L 31/0248
(Continued)

FOREIGN PATENT DOCUMENTS

JP 2012-247401 A 12/2012
JP 2014-081363 A 5/2014
WO WO-2020105706 A1 * 5/2020 ........... G01T 1/1612

OTHER PUBLICATIONS

Ushikura et al.—WO 2020/105706 A1—Google Patents English obtained Mar. 14, 2023 (Year: 2023).*

(Continued)

*Primary Examiner* — David P Porta
*Assistant Examiner* — Casey Bryant
(74) *Attorney, Agent, or Firm* — SOLARIS Intellectual Property Group, PLLC

(57) ABSTRACT

A radiography apparatus includes a substrate on which a pixel region in which a plurality of pixels that accumulate charges generated in response to incident radiations are arranged is formed on one surface of a flexible base material, a housing which accommodates the substrate and includes a front portion having an incident surface through which the radiations are incident on the substrate, a first buffer layer which is disposed between the front portion and the substrate in a thickness direction of the housing, the first buffer layer having an outer circumference provided inside the pixel region of the substrate in a plan view, and a structure which is disposed between the front portion and the substrate in the thickness direction at a position overlapping with the first buffer layer.

7 Claims, 9 Drawing Sheets

(56) References Cited

U.S. PATENT DOCUMENTS

2019/0110376 A1* 4/2019 Tagawa .............. H05K 7/20436
2022/0018976 A1* 1/2022 Bogumil ............. G01T 1/20189

OTHER PUBLICATIONS

English language translation of the following: Office action dated May 9, 2023 from the JPO in a Japanese patent application No. 2020-162672 corresponding to the instant patent application. This office action translation is submitted now in order to supplement the understanding of the cited reference which is being disclosed in the instant Information Disclosure Statement.

* cited by examiner

<ALTERNATIVE EMBODIMENT>

RADIOGRAPHY APPARATUS

CROSS REFERENCE TO RELATED APPLICATIONS

The present application claims priority under 35 U.S.C. § 119 to Japanese Patent Application No. 2020-162672 filed on Sep. 28, 2020. The above application is hereby expressly incorporated by reference, in its entirety, into the present application.

BACKGROUND OF THE INVENTION

1. Field of the Invention

The presently disclosed technology relates to a radiography apparatus.

2. Description of the Related Art

In the related art, a radiography apparatus that performs radiography for the purpose of medical diagnosis has been known. Such a radiography apparatus has a built-in radiation detector that detects radiations transmitted through a subject to generate a radiation image.

As the radiation detector, there are a direct conversion type in which the radiations are directly converted into charges and an indirect conversion type in which the radiations are once converted into visible light and the visible light is converted into the charge. In either type, the radiation detector comprises a substrate on which a plurality of pixels, which accumulate the charges generated based on the irradiation of the radiations, are formed.

As a base material of a substrate of such a radiation detector, using a flexible base material has been known. By using the flexible base material, a weight of the radiation detector can be reduced, and damage to the substrate can be prevented even in a case in which a load from the subject is applied at the time of imaging (see, for example, JP2014-081363A).

SUMMARY OF THE INVENTION

In a case in which the flexible base material is used as the base material of the substrate as in the radiation detector disclosed in JP2014-081363A, the following merit can be expected in addition to a merit of weight reduction as compared with the case in which relatively thick glass is used as the base material of the substrate. That is, the flexible base material is thin as compared with the glass in the related art. Therefore, while maintaining the thickness equal to or less than that of the glass in the related art, the substrate can be multilayered by providing another layer such as a layer for reinforcing the rigidity and a layer for improving heat dissipation property in addition to the flexible base material.

In a case in which the number of layers to be laminated increases due to multilayering, the gap between the layers increases, and thus the possibility that a foreign substance is mixed during the manufacture increases as compared with a case in which the glass in the related art is used as the base material.

In a case in which the load is applied to the radiation detector inside the radiography apparatus in a state in which the foreign substance exists between the layers, there is a risk that a pressure is applied to the substrate with the foreign substance as a base point and the substrate is deformed. In particular, since the flexible base material has lower rigidity than glass, it is easily deformed in accordance with an outer shape of the foreign substance. Therefore, in a case in which the flexible base material is used, a curvature of deformation of the substrate is smaller than that of the glass, so that strong pressure is applied to the pixels formed on the substrate, and the possibility of causing artifacts in the image increases.

Therefore, in a housing of the radiography apparatus, for example, it is conceivable to provide a buffer layer between an inner surface of the housing and the substrate to suppress the influence in a case in which the load is applied to the radiation detector in a state in which the foreign substance exists, but simply providing the buffer layer deteriorates the merit of thinning the flexible base material.

An object of the present disclosure is to provide a radiography apparatus which includes a built-in radiation detector having a substrate formed of a flexible base material, the radiography apparatus realizing thinning while being provided with a buffer layer.

A radiography apparatus according to an aspect of the present disclosure comprises a substrate on which a pixel region in which a plurality of pixels that accumulate charges generated in response to incident radiations are arranged is formed on one surface of a flexible base material, a housing which accommodates the substrate and includes a front portion having an incident surface through which the radiations are incident on the substrate, a first buffer layer which is disposed between the front portion and the substrate in a thickness direction of the housing, the first buffer layer having an outer circumference provided inside the pixel region of the substrate in a plan view, and a structure which is disposed between the front portion and the substrate in the thickness direction at a position overlapping with the first buffer layer.

It is preferable that the first buffer layer be joined to a substrate side via a joining member formed in a frame shape along the outer circumference.

Further, it is preferable that the first buffer layer be held on a substrate side, and the structure be held on a housing side.

Further, it is preferable that a thickness of the first buffer layer be equal to or more than 0.06 mm and equal to or less than 0.6 mm.

Further, the radiography apparatus may further comprise a drive circuit which outputs a drive signal for reading out the charges accumulated in the plurality of pixels, and a readout circuit which reads out the charges from the plurality of pixels in response to the drive signal, in which the structure is a protective member that protects at least a part of the drive circuit and the readout circuit from the radiations.

Further, it is preferable that the first buffer layer be a porous member.

Further, it is preferable that the radiography apparatus further comprise a second buffer layer on a surface side opposite to a surface side on which the first buffer layer is disposed with the substrate interposed therebetween.

Further, it is preferable that the second buffer layer be lead for backscattered ray absorption.

According to the presently disclosed technology, it is possible to provide the radiography apparatus which includes the built-in radiation detector having the substrate formed of the flexible base material, the radiography apparatus realizing thinning while being provided with the buffer layer.

DESCRIPTION OF THE PREFERRED EMBODIMENTS

Overall Configuration of Radiography Apparatus

Figure 1:
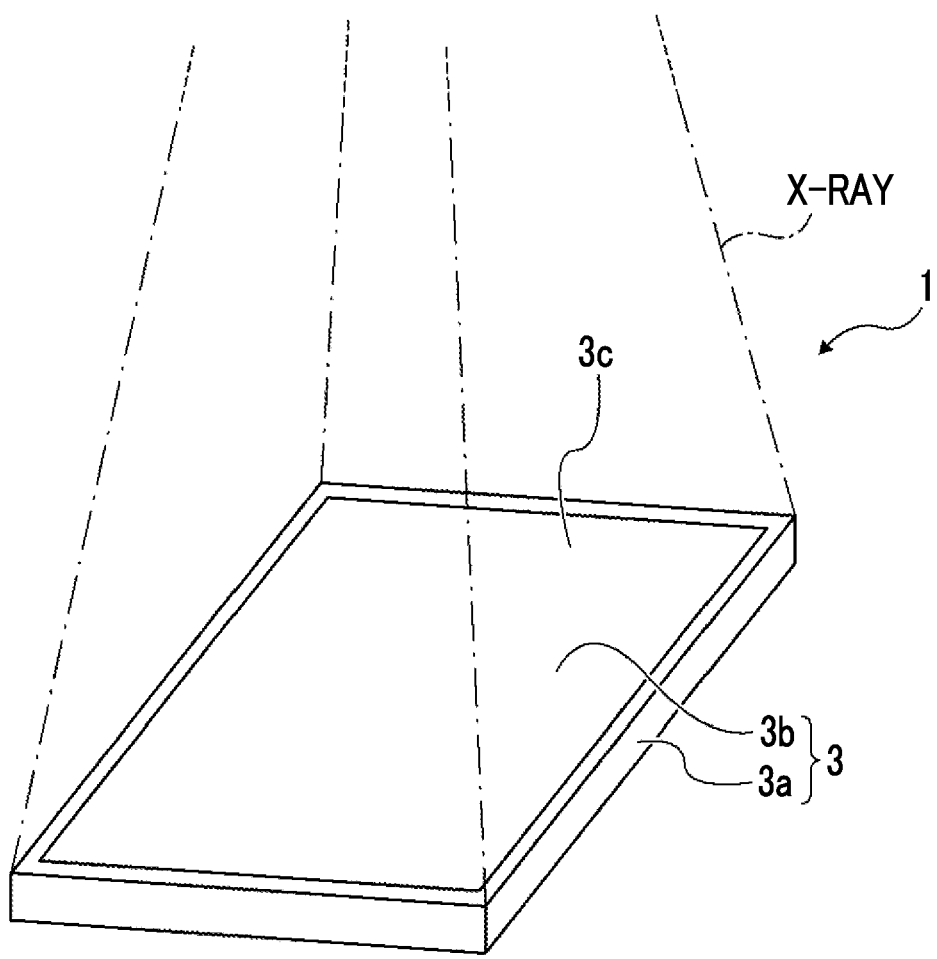
FIG. 1 is an external perspective view of a radiography apparatus.
Figure 2:
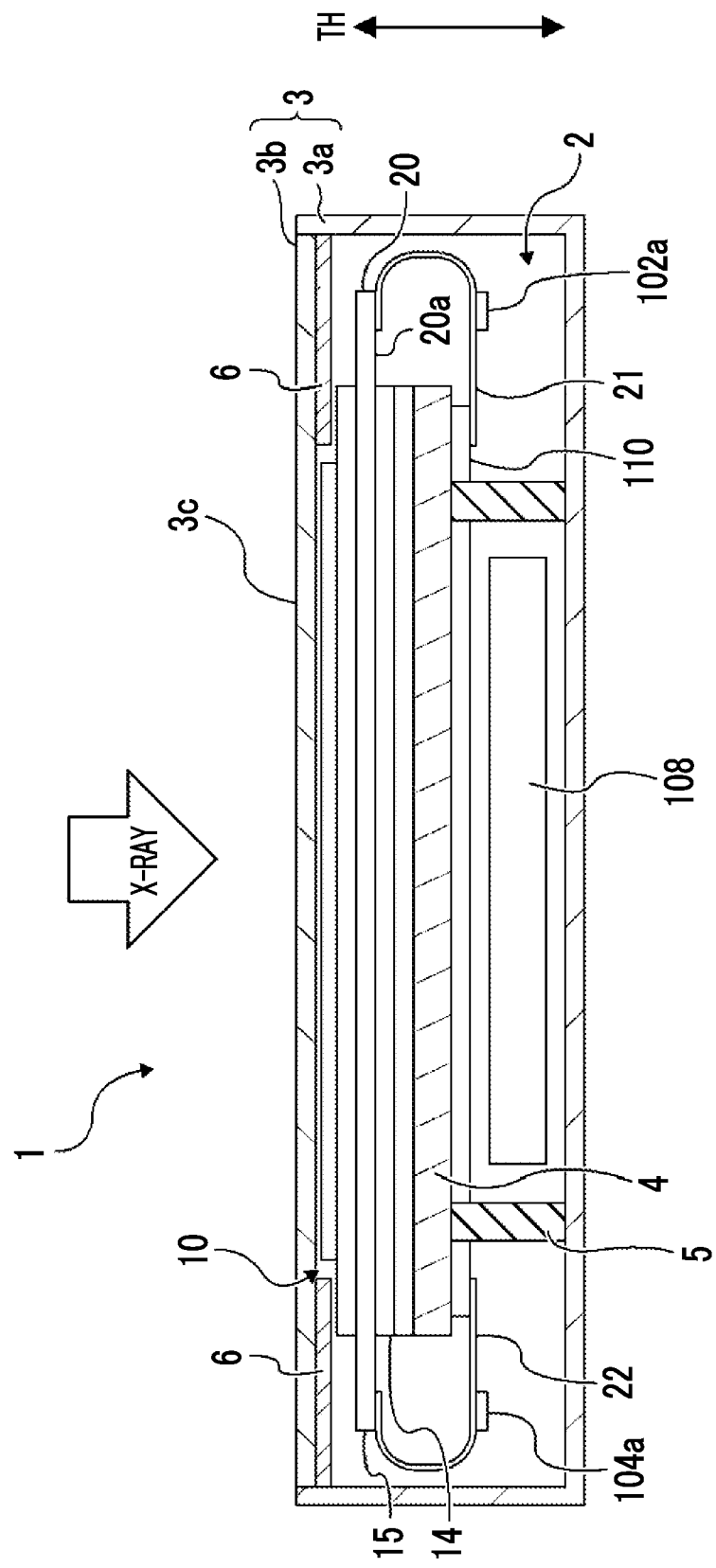
FIG. 2 is a schematic configuration diagram of the radiography apparatus.

FIG. 1 is an external perspective view of a radiography apparatus according to the presently disclosed technology, and FIG. 2 is a schematic configuration diagram of an inside thereof. As shown in FIGS. 1 and 2, a radiography apparatus 1 comprises a radiation detector 2 that detects X-rays, which is an example of a radiation, and a housing 3 that accommodates the radiation detector 2. The housing 3 has a front portion 3b including an incident surface 3c through which the radiations are incident inside, and a back portion 3a.

In the following description, for convenience, in a thickness direction TH of the radiography apparatus 1, the front portion 3b side (upper side in FIG. 1) of the housing 3 is defined as upward and the back portion 3a side (lower side in FIG. 1) is defined as downward.

The radiation detector 2 comprises a panel portion 10, a power supply unit 108, a control substrate 110, and the like. In the housing 3, the panel portion 10 is held on an upper surface of a base 4, and the control substrate 110 is held on a lower surface of the base 4.

The panel portion 10 comprises a conversion layer 14, a sensor substrate 15, and the like. The panel portion 10 of the present embodiment adopts an irradiation side sampling (ISS) type in which the X-rays are incident from the sensor substrate 15 side and the X-rays transmitted through the sensor substrate 15 reach the conversion layer 14, and the sensor substrate 15 and the conversion layer 14 are disposed in this order from the side on which the X-rays are incident. The sensor substrate 15 is a substrate in the presently disclosed technology.

The conversion layer 14 is a scintillator that converts the X-rays emitted to the panel portion 10 into light, and as an example, is a scintillator containing cesium iodide (CsI). It is preferable that such a scintillator contain cesium iodide added with thallium (CsI:Tl) or cesium iodide added with sodium (CsI:Na) having a light emission spectrum of 400 nm to 700 nm at the time of X-ray irradiation. Note that a light emission peak wavelength of CsI:Tl in a visible light region is 565 nm.

The sensor substrate 15 is a layer for detecting the light generated in the conversion layer 14. Details of the sensor substrate 15 will be described below.

The control substrate 110 controls the overall operation of the radiography apparatus 1. The sensor substrate 15 of the panel portion 10 is connected to the control substrate 110 via flexible print substrates 21 and 22. A gate driver integrated circuit (IC) 102a is mounted on the flexible print substrate 21. The gate driver IC 102a is one of circuit elements constituting a drive circuit 102 (see FIG. 3) used for driving the sensor substrate 15. Further, a charge amplifier IC 104a is mounted on the flexible print substrate 22. The charge amplifier IC 104a is one of the circuit elements constituting a readout circuit 104 (see FIG. 3) used for reading out a signal from the sensor substrate 15.

In the present embodiment, a back portion 3a of the housing 3 has a box shape with an opening formed on a front side, and a flat plate-shaped front portion 3b is fitted into the opening of the back portion 3a.

For the back portion 3a, for example, a light metal material such as aluminum and magnesium, or a resin material such as carbon fiber reinforced plastics (CFRP) is used in consideration of a strength-to-weight ratio and the like.

The X-rays transmitted through a subject are incident on the housing 3 through the incident surface 3c. The X-rays incident through the incident surface 3c are transmitted through the front portion 3b and incident on the panel portion 10 accommodated inside the housing 3. The front portion 3b is made of a material having excellent X-ray transmittance, and in consideration of the strength-to-weight ratio and the like, for example, the light metal material such as aluminum and magnesium, or the resin material such as carbon fiber reinforced plastics is used. Note that in the present embodiment, the front portion 3b including the incident surface 3c is formed as one member, but in the front portion 3b, the portion constituting the incident surface 3c and the other portion may be made of different materials.

The base 4 is attached to the back portion 3a via a support column 5. For the base 4 and the support column 5, for example, the light metal material such as aluminum and magnesium, or the resin material such as carbon fiber reinforced plastics is used in consideration of the strength-to-weight ratio and the like.

A protective member 6 that protects the gate driver IC 102a and the charge amplifier IC 104a, which are semiconductor elements, from the X-rays is fixed to a lower surface of the front portion 3b. For the protective member 6, a heavy metal material having excellent X-ray absorption property, such as copper, lead, tungsten, or molybdenum, can be used. The protective member 6 is a structure in the presently disclosed technology.

Configuration of Radiation Detector

Figure 3:
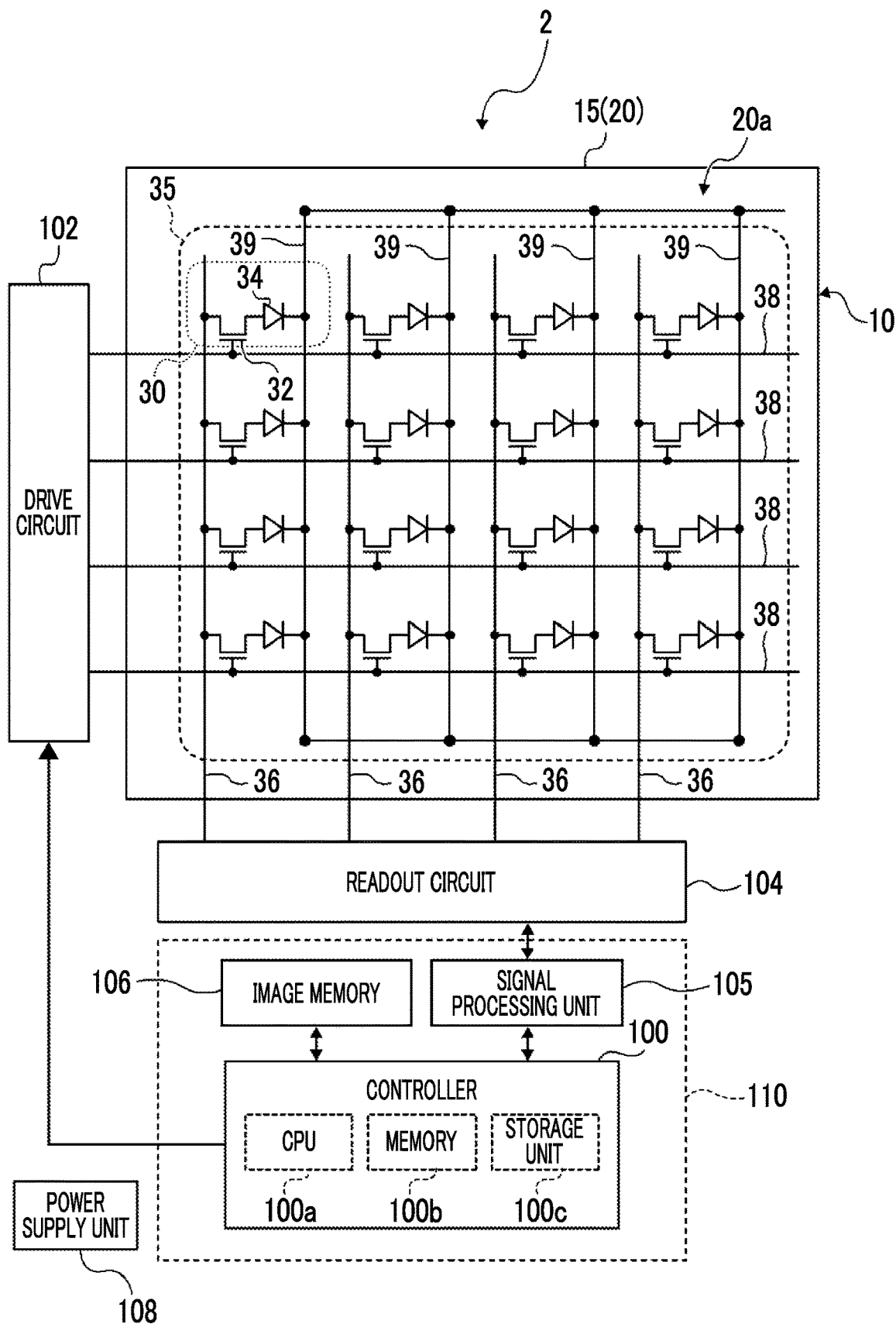
FIG. 3 is a schematic configuration diagram of an imaging unit of the radiography apparatus.

As shown in FIG. 3, the radiation detector 2 comprises the panel portion 10, a controller 100, the drive circuit 102, the readout circuit 104, an image memory 106, and the power supply unit 108.

The sensor substrate 15 of the panel portion 10 has a flexible base material 20. A pixel region 35 is formed on a lower surface 20a, which is one surface of the base material 20. The pixel region 35 is a region in which a plurality of pixels 30 that accumulate charges generated in response to the incident X-rays are arranged. In the present embodiment, the pixel region 35 is disposed substantially in the center of the base material 20. The pixel region 35 of the present embodiment is, to be exact, an effective pixel region. The effective pixel region refers to a region in which the pixels 30 that contribute to the formation of the radiation image are arranged among all the pixels 30 formed on the sensor substrate 15. The pixels 30 that contribute to the formation of the radiation image specifically refer to the pixels 30 in which the read out signal is used as a pixel value of the radiation image.

The base material 20 has flexibility, and for example, a resin sheet or glass containing a plastic such as polyimide (PI) can be used.

A thickness of the base material 20 need only be a thickness by which desired flexibility is obtained in accordance with the hardness of the material, the size of the sensor substrate 15, and the like. As an example of having flexibility, in the case of the rectangular base material 20 alone, there is a case in which in a state in which one side of the base material 20 is fixed, the base material 20 hangs down (lower than the height of the fixed side) by 2 mm or more by the gravity due to the weight of the base material 20 itself at a position 10 cm away from the fixed side.

A Young's modulus of the base material 20 is preferably equal to or more than 2 GPa and equal to or less than 85 GPa. Here, the measurement of the Young's modulus is performed by a resonance method in which a test piece at 20° C., which is a normal temperature, is vibrated and the natural vibration is measured to measure the Young's modulus. As a measurement device corresponding to the measurement of Young's modulus by the resonance method, for example, a JE-RT type manufactured by Nihon Techno-Plus Co., Ltd. can be used. Further, in a case in which the resin sheet is used as the base material 20, the thickness of the base material 20 is preferably equal to or more than 0.02 mm and equal to or less than 0.06 mm.

Each pixel 30 comprises a photoelectric conversion element 34 that generates charges in response to the light converted by the conversion layer 14 and accumulates the generated charges, and a thin film transistor (TFT) 32 that functions as a switching element for selecting the pixels 30 that read out the charges. The photoelectric conversion element 34 is, for example, a photodiode. A region in which a plurality of such pixels 30 are arranged is the pixel region 35.

In the pixel region 35, the plurality of pixels 30 are arranged in a two-dimensional matrix in a row direction (scanning wiring line 38 direction corresponding to a horizontal direction in FIG. 3) and a column direction (signal wiring line 36 direction corresponding to a vertical direction in FIG. 3). In FIG. 3, the arrangement of the pixels 30 is shown in a simplified manner, for example, 1024×1024 pixels 30 are arranged in the row direction and the column direction.

Further, in the panel portion 10, a plurality of the scanning wiring lines 38 for controlling a switching state (on and off) of the TFT 32, which are provided for each row of the pixels 30, a plurality of the signal wiring lines 36 for reading out the charges accumulated in the photoelectric conversion element 34, which are provided for each row of the pixels 30, are provided so as to intersect each other.

Each of the plurality of scanning wiring lines 38 is connected to the drive circuit 102. The drive circuit 102 drives the TFT 32 to control the switching state, and outputs the drive signal for reading out the charges accumulated in the TFT 32. As described above, the drive circuit 102 includes the gate driver IC 102a. The gate driver IC 102a includes the semiconductor elements and is mounted on the flexible print substrate 21 as shown in FIG. 1. Each of the plurality of scanning wiring lines 38 is connected to the gate driver IC 102a via the flexible print substrate 21. The gate driver IC 102a is connected to, via the flexible print substrate 21, the control substrate 110 on which the controller 100 is formed.

Further, each of the plurality of signal wiring lines 36 is connected to the readout circuit 104. The readout circuit 104 reads out the charges from the TFT 32 in response to the drive signal. The readout circuit 104 includes, in addition to the charge amplifier IC 104a that converts the charges output from the TFT 32 into a voltage signal, a multiplexer (not shown) for selecting the signal wiring line 36 for reading out the voltage signal, an analog-digital (AD) converter that converts the read out voltage signal into a digital signal, and the like. The circuit element constituting the readout circuit 104, such as the charge amplifier IC 104a, includes the semiconductor elements. As shown in FIG. 1, the charge amplifier IC 104a is mounted on the flexible print substrate 22. Each of the plurality of signal wiring lines 36 is connected to the charge amplifier IC 104a via the flexible print substrate 22. The charge amplifier IC 104a is connected to the control substrate 110 via the flexible print substrate 22.

In the control substrate 110, the controller 100, a signal processing unit 105, and the image memory 106 are provided. The signal processing unit 105 generates image data based on the digital signals corresponding to the charges read out from each pixel 30. The controller 100 is connected to the signal processing unit 105, and the image data output from the signal processing unit 105 is stored in the image memory 106 via the controller 100. The image memory 106 has a storage capacity capable of storing a predetermined number of the image data, and a plurality of number of the image data obtained by performing imaging a plurality of times is stored in the image memory 106.

The controller 100 comprises a central processing unit (CPU) 100a, a memory 100b including a read only memory (ROM), a random access memory (RAM), and the like, and a non-volatile storage unit 100c such as a flash memory. Examples of the controller 100 include a microcomputer or the like. The controller 100 controls the overall operation of the radiography apparatus 1.

Further, in the photoelectric conversion element 34 of each pixel 30, a common wiring line 39 is provided in a wiring line direction of the signal wiring line 36 in order to apply a bias voltage to each pixel 30. By connecting the common wiring line 39 to the power supply unit 108 outside the sensor substrate 15, the bias voltage is applied from the power supply unit 108 to each pixel 30.

In addition to applying the bias voltage to the photoelectric conversion element 34, the power supply unit 108 supplies power to various elements or various circuits such as the controller 100, the drive circuit 102, the readout circuit 104, the signal processing unit 105, and the image memory 106. Note that in FIG. 3, in order to avoid complications, the wiring lines connecting the power supply unit 108 with various elements or various circuits are omitted.

Configuration of Panel Portion

Figure 4:
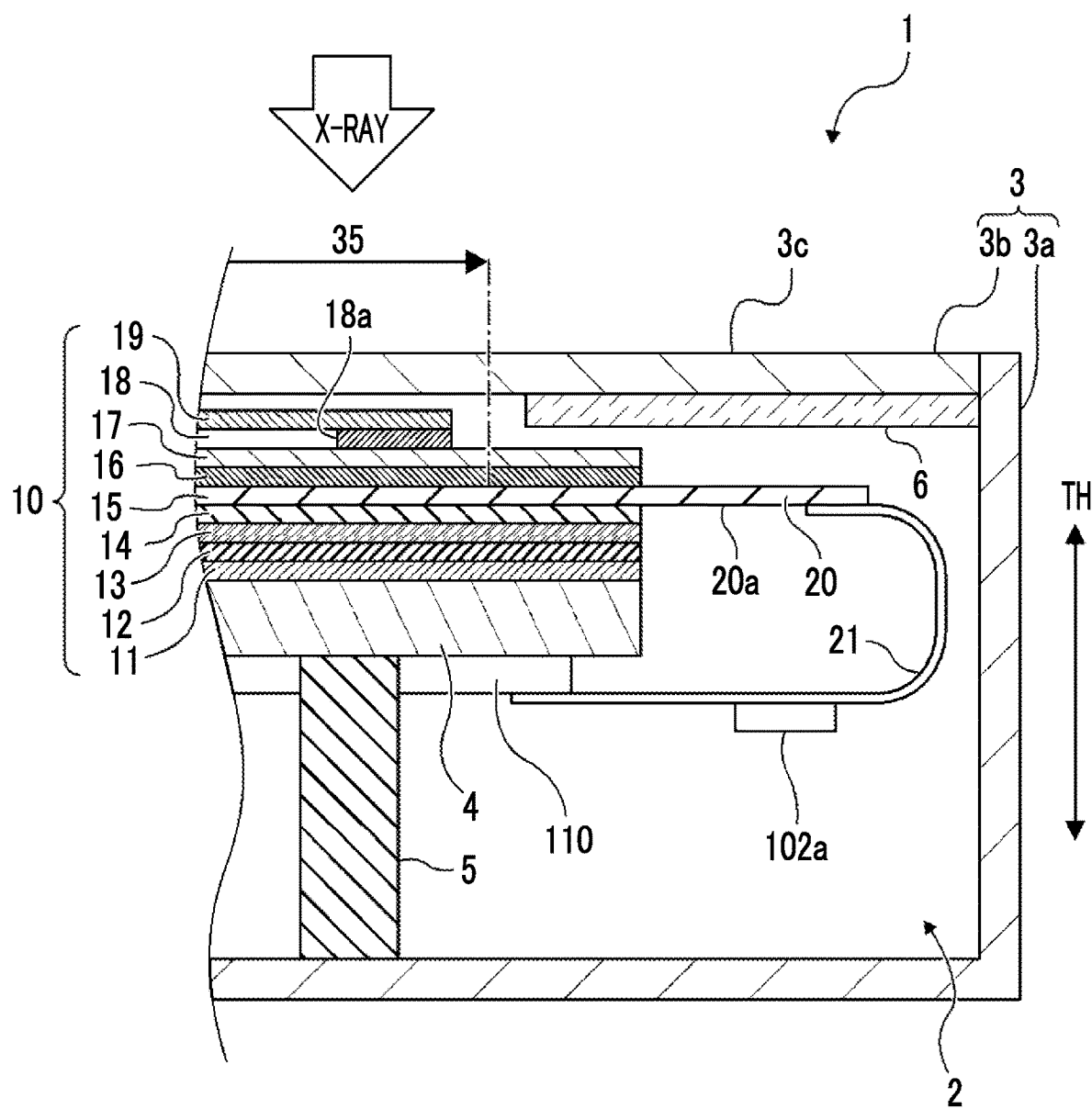
FIG. 4 is a schematic configuration diagram of a radiation detector of the radiography apparatus.

As shown in FIG. 4, the panel portion 10 comprises, as an example, a heat dissipation layer 11, a backscattered ray absorption layer 12, and a reinforcing layer 13 on the lower surface side of the conversion layer 14 and the sensor substrate 15. Further, the panel portion 10 comprises a protective layer 16, a reinforcing layer 17, a joining layer 18, and a buffer layer 19 on the upper surface side of the conversion layer 14 and the sensor substrate 15. That is, the panel portion 10 has a configuration in which the heat dissipation layer 11, the backscattered ray absorption layer 12, the reinforcing layer 13, the conversion layer 14, the sensor substrate 15, the protective layer 16, the reinforcing layer 17, the joining layer 18, and the buffer layer 19 are laminated in this order from the base 4 side.

The heat dissipation layer 11 is a layer for dissipating heat accumulated in the panel portion 10, and is made of, for example, a resin material such as carbon fiber reinforced plastics (CFRP).

The backscattered ray absorption layer 12, which is made of lead (Pb), is a layer for absorbing scattered rays generated by the X-rays transmitted through the conversion layer 14 and the sensor substrate 15. Lead is a relatively soft material among the heavy metal materials having excellent X-ray absorption property. Further, the backscattered ray absorption layer 12 made of lead, which is a relatively soft material, in a case in which the load is applied to the radiography apparatus 1 in a state in which a foreign substance exists, can absorb the pressure from the foreign substance by the deformation of the backscattered ray absorption layer 12 itself to suppress the influence of the foreign substance on the sensor substrate 15. That is, the backscattered ray absorption layer 12 also functions as a buffer layer (second buffer layer in the presently disclosed technology) for suppressing the influence of the foreign substance on the sensor substrate 15.

Here, examples of the foreign substance inside the radiography apparatus 1 include a foreign substance present between the housing 3 and the panel portion 10, a foreign substance mixed inside the panel portion 10 during the manufacture of the panel portion 10, and the like. Specifically, the foreign substance is dust, powder dust, or the like. Further, a diameter of the foreign substance is considered to be mainly equal to or less than 0.5 mm.

The reinforcing layer 13 is a layer for reinforcing the strength of the sensor substrate 15 formed of the flexible base material 20, and is made of plastic as an example. Examples of the plastic used as the material of the reinforcing layer 13 include at least one of polycarbonate (PC), polyethylene terephthalate (PET), styrol, acrylic, polyacetal, nylon, polypropylene, acrylonitrile butadiene styrene (ABS), engineering plastic, or polyphenylene ether.

The protective layer 16 is a layer for moisture-proofing and preventing antistatic of the pixel region 35 of the sensor substrate 15. As the protective layer 16, for example, an insulating moisture-proof sheet such as an Alpet (registered trademark) sheet, a Parylene (registered trademark) sheet, and a polyethylene terephthalate sheet is used.

The reinforcing layer 17 is a layer for reinforcing the strength of the sensor substrate 15 formed of the flexible base material 20, and is made of plastic. Examples of the plastic used as the material of the reinforcing layer 13 include at least one of PC, PET, styrol, acrylic, polyacetal, nylon, polypropylene, ABS, engineering plastic, or polyphenylene ether.

Figure 5:
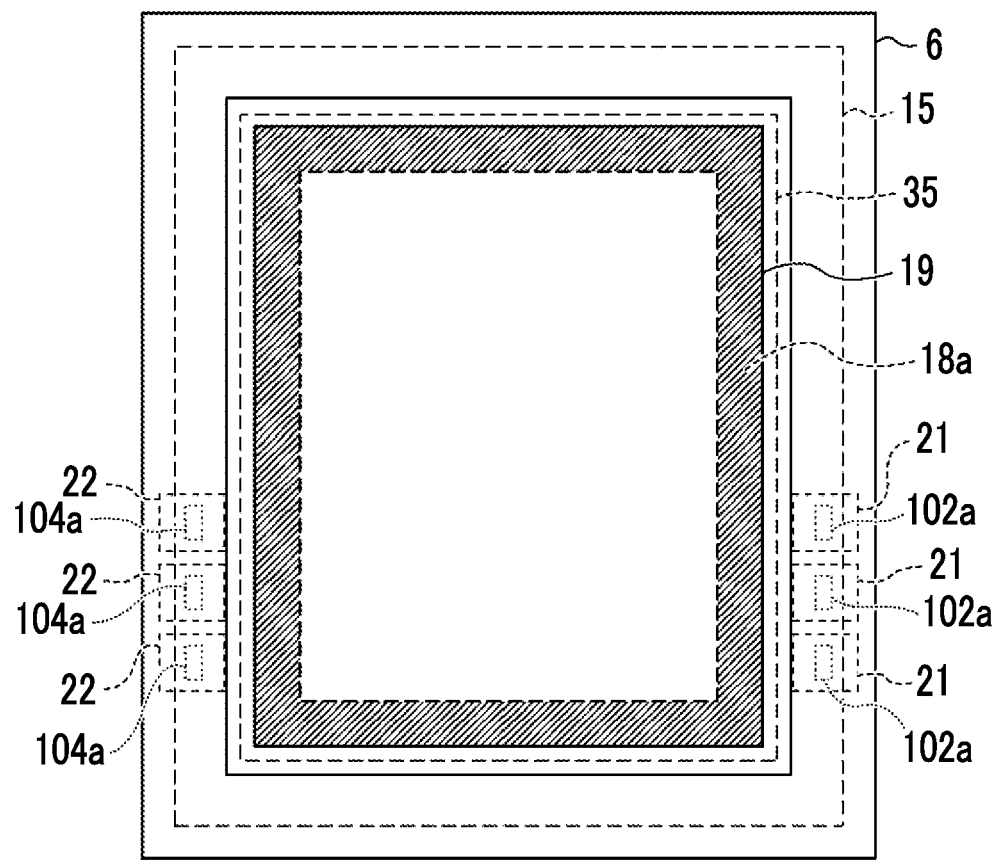
FIG. 5 is a top view of the radiation detector and a protective member.

FIG. 5 is a top view of the panel portion 10 and the protective member 6. As shown in FIGS. 4 and 5, the joining layer 18 is a layer for joining the reinforcing layer 17 and the buffer layer 19, and includes a joining member 18a formed in a frame shape along an outer circumference of the buffer layer 19. As an example, double-sided tape is used as the joining member 18a. In FIG. 5, although three gate driver ICs 102a and three charge amplifier ICs 104a are shown, actually three or more are provided. In FIG. 5, it is omitted in order to avoid complication of the drawing.

The buffer layer 19 (first buffer layer in the presently disclosed technology) is disposed between the front portion 3b and the sensor substrate 15 as an example of the substrate in the thickness direction TH of the housing 3. The buffer layer 19 is a layer for suppressing the influence of the foreign substance on the sensor substrate 15, and a porous member such as a nonwoven fabric or a sponge can be used.

Further, a thickness of the buffer layer 19 is preferably equal to or more than 0.06 mm and equal to or less than 0.6 mm. In the present embodiment, as an example, a nonwoven fabric having a thickness of 0.5 mm is used. As shown in FIG. 5, the outer circumference of the buffer layer 19 is provided inside the pixel region 35 of the sensor substrate 15 in a plan view.

The protective member 6 that protects the gate driver IC 102a and the charge amplifier IC 104a, which include the semiconductor elements, from the X-rays is disposed in the outer circumferential portion of the buffer layer 19 of the panel portion 10. The protective member 6 is disposed between the front portion 3b and the sensor substrate 15 at a position overlapping with the buffer layer 19 in the thickness direction TH of the housing 3. In addition, the protective member 6 is provided outside the pixel region 35 of the sensor substrate 15.

Operation and Effect

The radiography apparatus 1 according to the present embodiment comprises the panel portion 10 including the sensor substrate 15 in which the plurality of pixels that accumulate the charges generated based on the irradiation of the X-rays are formed in the pixel region 35 on one surface of the flexible base material 20, the housing 3 including the back portion 3a which accommodates the panel portion 10 and the front portion 3b which is disposed on the incident surface through which the X-rays are incident on the sensor substrate 15, and the buffer layer 19 which is the first buffer layer disposed between the front portion 3b and the sensor substrate 15, in which the buffer layer 19 is provided inside of the sensor substrate 15 and the pixel region 35 and comprises the protective member 6 which is a structure disposed between the front portion 3b and the sensor substrate 15 in the thickness direction TH of the buffer layer 19 at a position overlapping with the buffer layer 19.

Since the flexible base material 20 is used as the base material of the sensor substrate 15, the weight of the panel portion 10 can be reduced, and even in a case in which the load from the subject is applied at the time of imaging, the sensor substrate 15 itself can bend to prevent the sensor substrate 15 from being damaged.

Further, the sensor substrate 15 is an example of the substrate in which the pixel region 35 is formed on one surface of the flexible base material 20. Since the flexible base material 20 is soft, there is a problem that it is easily affected by the foreign substance. In order to handle such a problem, the radiography apparatus 1 according to the present embodiment comprises the buffer layer 19 which is the first buffer layer between the front portion 3b and the sensor substrate 15. Therefore, for example, even in a case in which the subject is in close contact with the housing 3 of the radiography apparatus 1 at the time of imaging and the load is applied to the panel portion 10 inside the housing 3 in a state in which the foreign substance exists, the buffer layer 19 can absorb the pressure from the foreign substance to suppress the influence of the foreign substance on the sensor substrate 15. The buffer layer 19 is particularly effective for the foreign substance positioned above the sensor substrate 15, such as the foreign substance present between the front portion 3b and the buffer layer 19, the foreign substance present between the buffer layer 19 and the reinforcing layer 17.

Further, in the presently disclosed technology, the buffer layer 19 is disposed between the front portion 3b and the sensor substrate 15 in the thickness direction TH of the housing 3, and the outer circumference is provided inside the pixel region 35 of the sensor substrate 15 in a plan view.

Further, in the presently disclosed technology, the structure (protective member 6 in the present embodiment) disposed between the front portion 3b and the sensor substrate 15 at a position overlapping with the buffer layer 19 is provided in the thickness direction TH of the housing 3. As described above, by accommodating the outer circumference of the buffer layer 19 inside the pixel region 35, in the housing 3, a relatively large space for disposing the structure around the buffer layer 19 is secured. Further, since the secured space is around the buffer layer 19, even in a case in which the structure is disposed in this space, the increase in the thickness of the housing 3 due to the disposition of the structure is small. As a result, it is possible to realize the radiography apparatus 1, which realizes thinning while being provided with the buffer layer 19.

Further, as described above, the sensor substrate 15 is a TFT type having the flexible base material 20. The TFT type substrate has an advantage that the area can be easily increased as compared with a complementary metal oxide semiconductor (CMOS) type substrate using a metal material as the base material, but as described above, the flexible base material 20 is soft, and thus it is easily affected by the foreign substance. Therefore, the presently disclosed technology in which the buffer layer 19 is provided is particularly effective for the TFT type substrate having the flexible base material 20 as compared with the CMOS type substrate.

Also, as shown in FIG. 5, the buffer layer 19 is joined to the reinforcing layer 17 on the sensor substrate 15 side via the joining member 18a formed in a frame shape along the outer circumference. Therefore, entering of the foreign substance between the buffer layer 19 and the pixel region 35 from the outside of the panel portion 10 can be suppressed.

Figure 6:
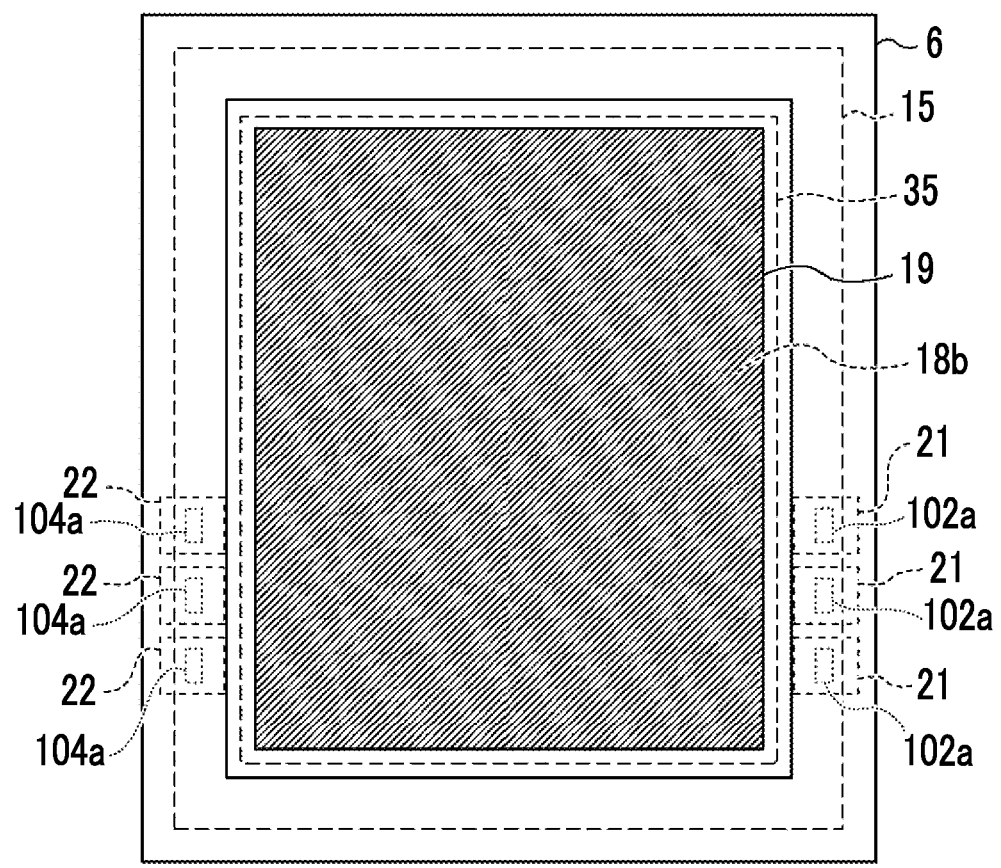
FIG. 6 is a top view of the radiation detector and the protective member, which shows a different disposition form of a joining member.

In addition, for example, as shown in FIG. 6, it is also possible to provide a joining member 18b corresponding to the entire surface of the buffer layer 19. However, as shown in FIG. 5, in a case in which the joining member 18a is provided corresponding to only a part of the buffer layer 19, an amount of the joining member 18a can be small as compared with a case in which the joining member 18b is provided corresponding to the entire surface of the buffer layer 19. Also, the aspect shown in FIG. 5 can facilitate the manufacture of the panel portion 10.

Figure 7:
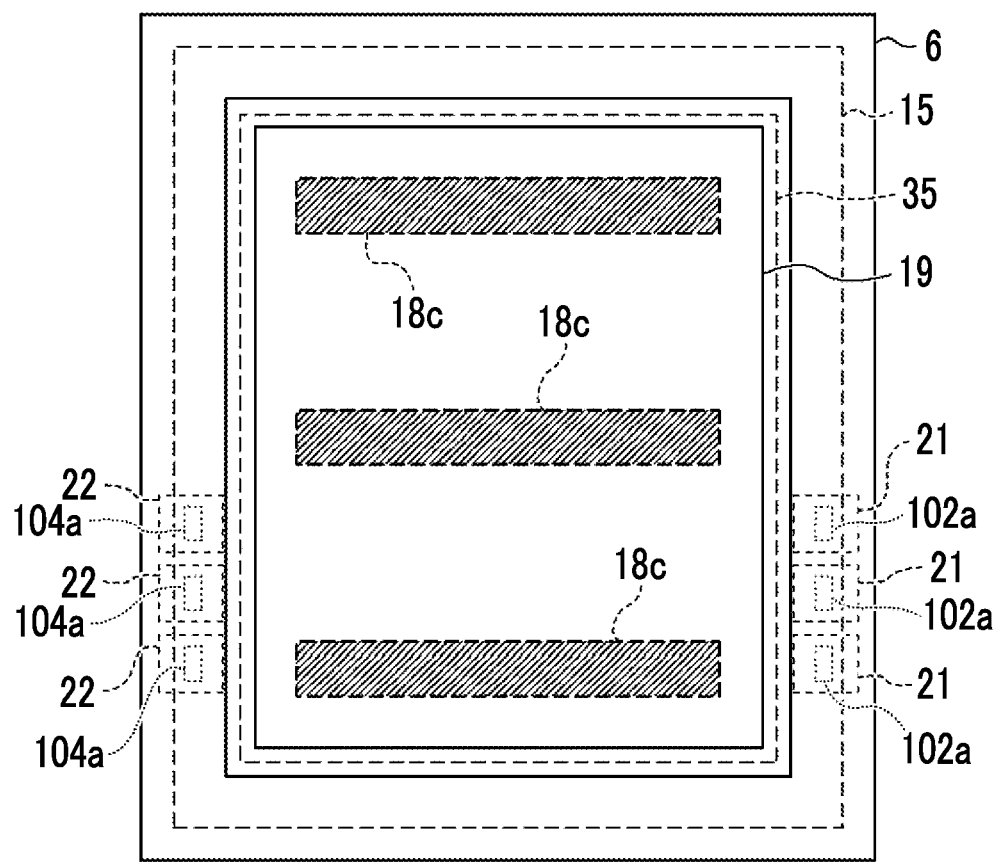
FIG. 7 is a top view of the radiation detector and the protective member, which shows a different disposition form of the joining member.

Further, in a case in which the joining member is provided corresponding to only a part of the buffer layer 19, for example, a plurality of strip-shaped joining members 18c can be arranged in parallel as shown in FIG. 7. However, in the aspect of FIG. 7, there is a risk that the foreign substance enters between the buffer layer 19 and the pixel region 35 from a portion in which the joining member 18c is not provided. On the other hand, as described above, in the aspect shown in FIG. 5, the joining member 18a is formed in a frame shape along the outer circumference of the buffer layer 19 to seal a portion between the buffer layer 19 and the reinforcing layer 17, and thus entering of the foreign substance to the panel portion 10 can be suppressed. Note that in a case in which the joining member 18a is provided in a frame shape, it may be an integrally formed frame-shaped joining member, or a linear joining member may be combined in a frame shape.

Also, the buffer layer 19 is held on the sensor substrate 15 side, and the protective member 6 which is the structure is held on the front portion 3b on the housing 3 side. It is considered that the inner surface of the front portion 3b has less unevenness than the sensor substrate 15 side. Therefore, it is easier to provide the protective member 6 on the front portion 3b as compared with a case in which the protective member 6 is provided on the sensor substrate 15 side.

Further, in a case in which the thickness of the buffer layer 19 is less than 0.06 mm, the pressure from the foreign substance cannot be completely absorbed in a case in which the load is applied to the panel portion 10 in a state in which the foreign substance exists, and it is difficult to suppress the influence of the foreign substance on the sensor substrate 15. As a result, there is a risk that artifacts occur in an X-ray image. Further, in the radiography apparatus 1 according to the present embodiment, since the buffer layer 19 is provided inside the pixel region 35 of the sensor substrate 15, in a case in which the thickness of the buffer layer 19 exceeds 0.6 mm, an end part of the buffer layer 19 is easily reflected in the X-ray image acquired by the radiography apparatus 1. In the radiography apparatus 1 according to the present embodiment, since the thickness of the buffer layer 19 is equal to or more than 0.06 mm and equal to or less than 0.6 mm, the end part of the buffer layer 19 can be hard to be reflected in the X-ray image while suppressing the influence of the foreign substance.

Further, in the radiography apparatus 1 according to the present embodiment, the drive circuit 102 includes the gate driver IC 102a, and the readout circuit 104 includes the charge amplifier IC 104a. The gate driver IC 102a and the charge amplifier IC 104a also include the semiconductor elements as the circuit element. By providing the protective member 6 that protects at least a part of the drive circuit 102 and the readout circuit 104 from the X-rays as the structure of the present embodiment, malfunctions, failures, and deteriorations of the drive circuit 102 and the readout circuit 104 can be suppressed.

The buffer layer 19 and the protective member 6 need to be disposed at certain intervals to prevent contact. In the radiography apparatus 1 according to the present embodiment, the outer circumference of the buffer layer 19 is provided inside the pixel region 35 of the sensor substrate 15, and the protective member 6 can be disposed in the vicinity of the outer circumferential portion of the buffer layer 19 between the front portion 3b and the sensor substrate 15. That is, the protective member 6 can be disposed in a wide range from the outer circumferential portion of the housing 3 to the inside.

Figure 8:
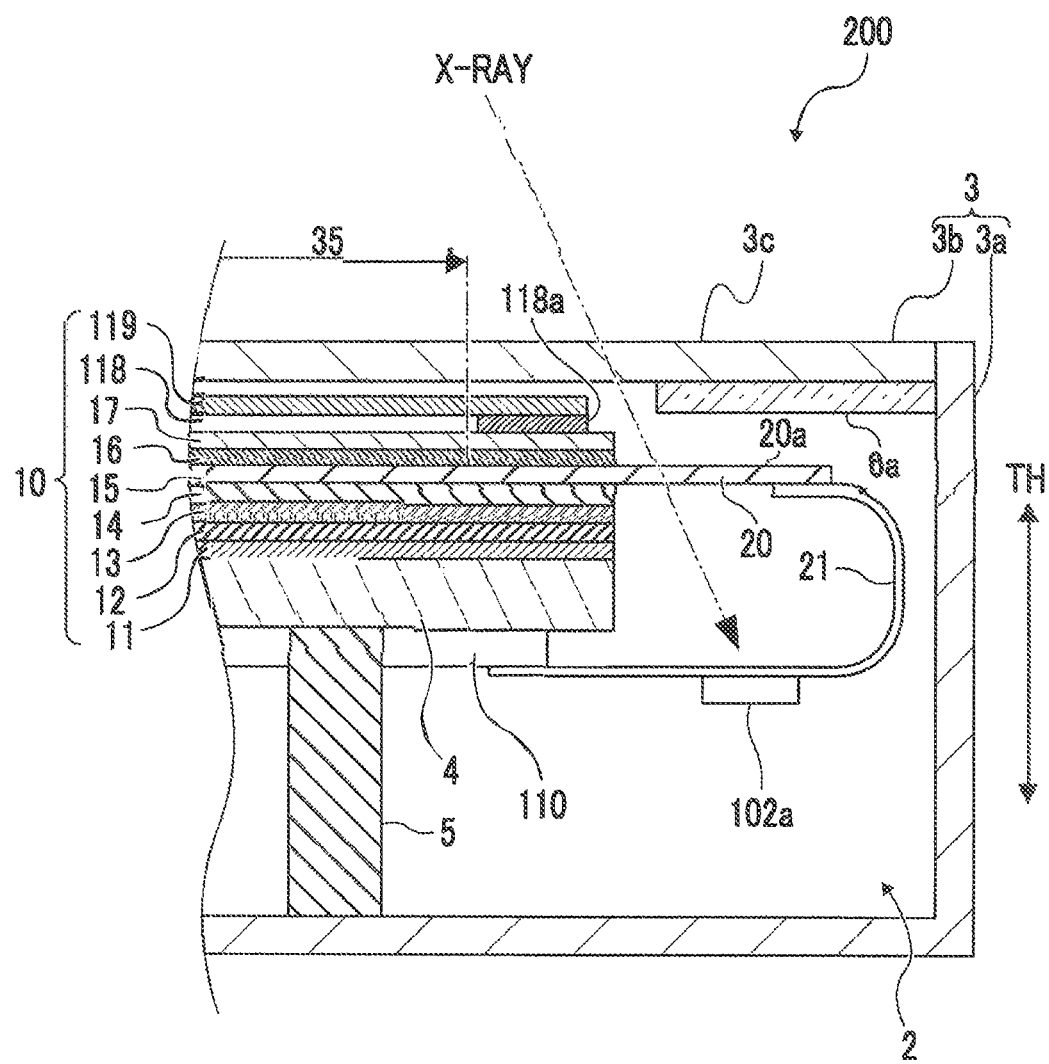
FIG. 8 is a diagram showing a state in which X-rays are incident from an unexpected direction in a radiography apparatus in the related art.

A radiography apparatus 200 shown in FIG. 8 is a alternative embodiment in which the outer circumference of the buffer layer 119 and the joining layer 118 are positioned outside the pixel region 35. In the radiography apparatus 1 according to the present embodiment shown in FIG. 9, the end part of the protective member 6 on the panel portion 10 side overlaps with a part of the panel portion 10 in a plan view. On the other hand, in the radiography apparatus 200 of the alternative embodiment, the end part of the protective member 6a on the panel portion 10 side is spaced from the panel portion 10 in a plan view.

Figure 9:
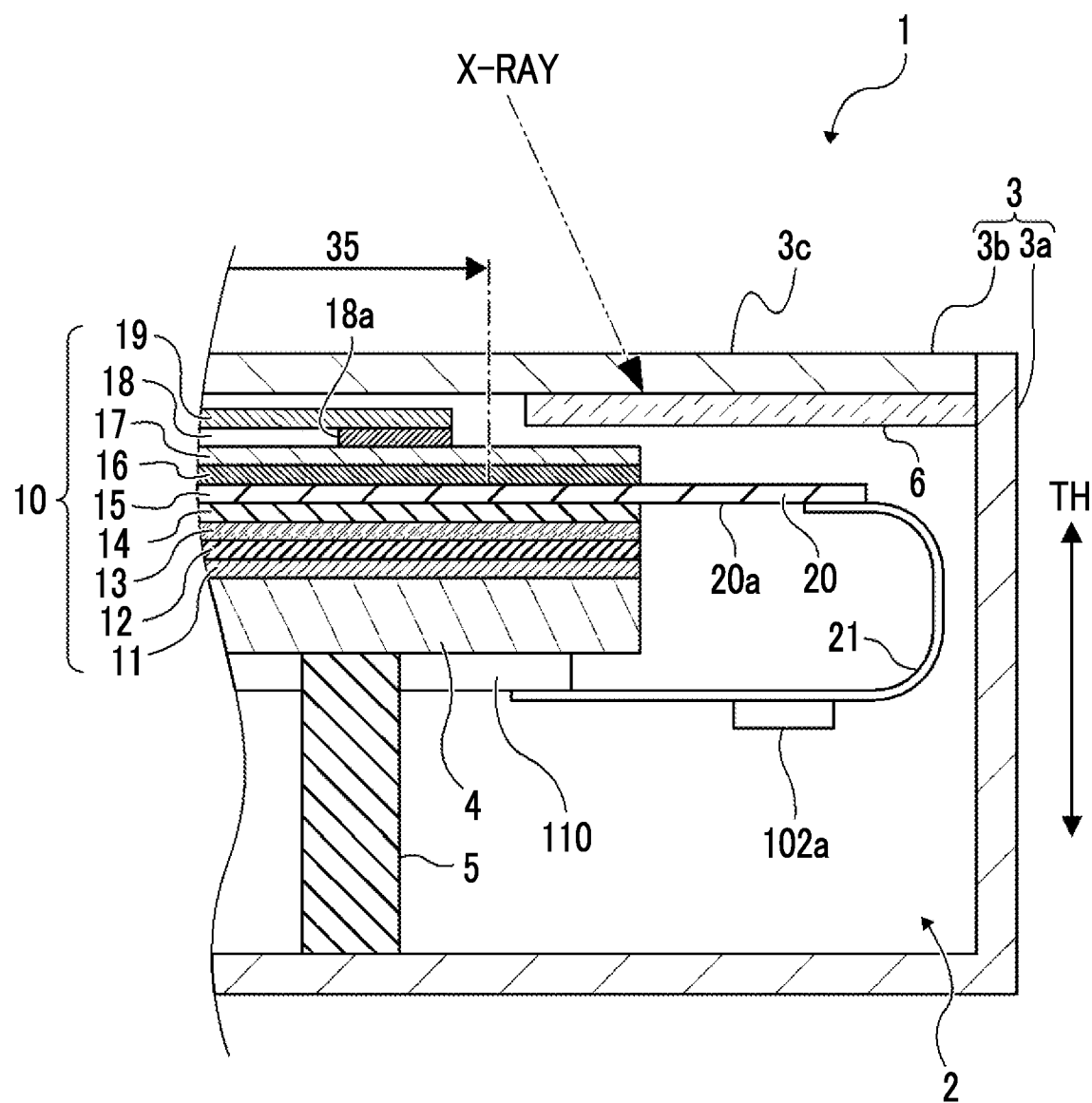
FIG. 9 is a diagram showing a state in which X-rays are incident from an unexpected direction in the radiography apparatus.

Since the X-rays are emitted from a focal point of a radiation source, as shown in FIGS. 8 and 9, an irradiation angle is oblique toward the outside from the center of the panel portion 10. Further, depending on the imaging purpose, so-called oblique incidence imaging in which the X-rays are obliquely incident on the pixel region 35 may be performed, and in this case, the irradiation angle of the X-rays on the outer circumference of the panel portion 10 is more oblique. In FIGS. 8 and 9, the irradiation angles of the X-rays are the same.

In such a case, in the radiography apparatus 200 of the alternative embodiment shown in FIG. 8, the X-rays are transmitted through the gap between a protective member 6a and the panel portion 10, and there is a risk that the gate driver IC 102a and the like are irradiated with X-rays.

On the other hand, in the radiography apparatus 1 according to the present embodiment, as shown in FIG. 9, the buffer layer 19 is provided inside the pixel region 35 of the sensor substrate 15, and the end part of the protective member 6 on the panel portion 10 side can be further brought closer to the pixel region 35 side as compared with the radiography apparatus 200 of the alternative embodiment. Therefore, it is easy to prevent the gate driver IC 102a or the like, which is the semiconductor element, from being irradiated with the X-rays.

Further, the buffer layer 19 is made of a nonwoven fabric which is the porous member. In a case in which the load is applied to the panel portion 10 inside the radiography apparatus 1, the foreign substance present between the front portion 3b and the buffer layer 19 and the foreign substance present between the buffer layer 19 and the reinforcing layer 17 are taken into holes of the porous member. Further, even in a case in which the foreign substance is mixed inside the panel portion 10, the soft porous member absorbs the pressure, which is applied to the sensor substrate 15 via the foreign substance. Therefore, even in a case in which the foreign substance is present inside the radiography apparatus 1, the influence of the foreign substance on the sensor substrate 15 can be suppressed.

Further, the radiography apparatus 1 according to the present embodiment comprises the backscattered ray absorption layer 12 which is the second buffer layer on a surface side opposite, across the sensor substrate 15, to a surface side on which the buffer layer 19 is disposed. Therefore, even in a case in which the load is applied to the internal panel portion 10 inside the radiography apparatus 1 in a state in which the foreign substance exists, the backscattered ray absorption layer 12 can absorb the pressure from the foreign substance to suppress the influence of the foreign substance on the sensor substrate 15. The backscattered ray absorption layer 12 is particularly effective for the foreign substance positioned below the sensor substrate 15, such as foreign substance present between the heat dissipation layer 11 and the base 4.

Further, the backscattered ray absorption layer 12 is made of lead, which is particularly soft among the heavy metal materials having excellent X-ray absorption property, and the backscattered ray absorption layer 12 functions as the second buffer layer. Therefore, as compared with the case in which the backscattered ray absorption layer and the second buffer layer are individually formed, the cost can be suppressed and the panel portion 10 is also advantageous in thinning.

MODIFICATION EXAMPLE

In the presently disclosed technology, it is possible to appropriately combine the above embodiment with various modification examples.

For example, in the above embodiment, the aspect in which the pixels 30 are arranged in a two-dimensional matrix as shown in FIG. 3 has been described, but the present invention is not limited to this, and for example, it may be a one-dimensional array or a honeycomb array. Also, the shape of the pixel is not limited, and it may be a rectangle or a polygon such as a hexagon. Further, it is needless to say that the shape of the pixel region 35 is not limited.

Further, the panel portion 10 is not limited to the ISS type, and may be a penetration side sampling (PSS) type in which the conversion layer and the sensor substrate are disposed in this order from the side on which the X-rays are incident at the time of imaging.

Further, the layer configuration of the panel portion 10 is not limited to the above embodiment, and some or all of the layers except for the conversion layer 14, the sensor substrate 15, the joining layer 18, and the buffer layer 19 may be removed, or other layers not described in the above embodiment may be added separately.

Further, the panel portion 10 is not limited to the indirect conversion type in which the X-rays are once converted into visible light and then converted into the charges as described in the above embodiment, but may also be the direct conversion type in which the X-rays are directly converted into the charges.

Further, the protective member 6, which is the structure, is not limited to the aspect in which the protective member 6 is formed in a frame shape over the entire outer circumferential portion of the buffer layer 19, and for example, may be provided only a part of the outer circumferential portion of the buffer layer 19, such as providing only in the vertical direction in FIG. 5.

Further, the structure is not limited to the protective member 6 that protects the semiconductor elements from the X-rays, and any structure may be used as long as it is a structure required for the radiography apparatus 1, such as an illumination component or a thick portion for improving the rigidity of the housing.

The contents described and shown above are the detailed description of the parts relating to the presently disclosed technology, and are merely an example of the presently disclosed technology. For example, the above description of the configuration, the function, the operation, and the effect are the description of examples of the configuration, the function, the operation, and the effect of the parts relating to the presently disclosed technology. Therefore, it should be noted that unnecessary parts may be deleted, new elements may be added, or replacements may be made with respect to the contents described and shown above within a range that does not deviate from the gist of the presently disclosed technology. In addition, in order to avoid complications and facilitate understanding of the parts relating to the presently disclosed technology, in the contents described and shown above, the description of common general knowledge and the like that do not particularly require explanation for enabling the implementation of the presently disclosed technology are omitted.

All of the documents, the patent applications, and the technical standards described in the present specification are incorporated in the present specification by reference to the same extent as a case in which each of the document, the patent application, and the technical standard is specifically and individually noted to be incorporated by reference.

EXPLANATION OF REFERENCES

1: radiography apparatus
2: radiation detector
3: housing
3a: back portion
3b: front portion
4: base
5: support column
6, 6a: protective member
10: panel portion
11: heat dissipation layer
12: backscattered ray absorption layer 13: reinforcing layer
14: conversion layer
15: sensor substrate
16: protective layer
17: reinforcing layer
18: joining layer
18a, 18b, 18c: joining member
19, 19a: buffer layer
20: base material
21: flexible print substrate
22: flexible print substrate
30: pixel
32: switching element
34: sensor unit
35: pixel region
36: signal wiring line
38: scanning wiring line
39: common wiring line
100: controller
100a: CPU
100b: memory
100c: storage unit
102: drive circuit
102a: gate driver IC
104: readout circuit
104a: charge amplifier IC
105: signal processing unit
106: image memory
108: power supply unit
110: control substrate
200: radiography apparatus

What is claimed is:

1. A radiography apparatus comprising:
a substrate on which a pixel region in which a plurality of pixels that accumulate charges generated in response to incident radiations are arranged is formed on one surface of a flexible base material;
a housing which accommodates the substrate and includes a front portion having an incident surface through which the radiations are incident on the substrate;
a first buffer layer which is disposed between the front portion and the substrate in a thickness direction of the housing, the first buffer layer having an outer circumference provided inside the pixel region of the substrate in a plan view; and
a structure which is disposed between the front portion and the substrate overlaps the first buffer layer in the thickness direction;
wherein the first buffer layer is joined to a substrate side via a joining member formed in a frame shape along the outer circumference.

2. The radiography apparatus according to claim 1,
wherein the first buffer layer is held on a substrate side, and
the structure is held on a housing side.

3. The radiography apparatus according to claim 1,
wherein a thickness of the first buffer layer is equal to or more than 0.06 mm and equal to or less than 0.6 mm.

4. The radiography apparatus according to claim 1, further comprising:
a drive circuit which outputs a drive signal for reading out the charges accumulated in the plurality of pixels; and
a readout circuit which reads out the charges from the plurality of pixels in response to the drive signal,
wherein the structure is a protective member that protects at least a part of the drive circuit and the readout circuit from the radiations.

5. The radiography apparatus according to claim 1,
wherein the first buffer layer is a porous member.

6. The radiography apparatus according to claim 1, further comprising:
a second buffer layer that is provided on an opposite side of the substrate from a side where the first buffer layer is provided.

7. The radiography apparatus according to claim 6,
wherein the second buffer layer is lead (Pb) for backscattered ray absorption.

* * * * *